United States Patent
Geluk

Patent Number: 5,608,777
Date of Patent: Mar. 4, 1997

[54] SLIT RADIOGRAPHY APPARATUS

[75] Inventor: Ronald J. Geluk, PL Nootdorp, Netherlands

[73] Assignee: B.V. Optische Industrie "De Oude Delft", XE Delft, Netherlands

[21] Appl. No.: 910,251
[22] PCT Filed: Jan. 28, 1991
[86] PCT No.: PCT/EP91/00174
 § 371 Date: Jul. 13, 1992
 § 102(e) Date: Jul. 13, 1992
[87] PCT Pub. No.: WO91/11143
 PCT Pub. Date: Aug. 8, 1991

[30] Foreign Application Priority Data

Feb. 1, 1990 [NL] Netherlands .................. 9000250

[51] Int. Cl.$^6$ .................................................. G21K 5/10
[52] U.S. Cl. .................................. 378/146; 378/145
[58] Field of Search .............................. 378/146

[56] References Cited

U.S. PATENT DOCUMENTS 5,058,149 10/1991 Vlasbloem .................. 378/146

*Primary Examiner*—Craig E. Church
*Attorney, Agent, or Firm*—Louis E. Marn

[57] ABSTRACT

A slit radiography apparatus is provided with an absorption device comprising electrically controllable piezoelectric tongues. Upper and/or lower deflections of the tongues are limited to a maximum by trips outside the X-ray fan beam. More than one strip can be present as seen in the length direction from the fixed ends of the tongues. Thus deflections of the tongues are limited and great phase changes in the control signals without resultant oscillations can take place during the time the tongue are restricted in their movement by the strip.

5 Claims, 2 Drawing Sheets

SLIT RADIOGRAPHY APPARATUS

The invention relates to a slit radiography apparatus comprising an X-ray source, an X-ray detector for sensing radiation passing through a body to be radiographed, a slit diaphragm positioned between said X-ray source and said body for forming a substantially planar X-ray beam, means for scanning said body with said planar X-ray beam in a direction transverse to a longitudinal direction of a slit of said slit diaphragm, an absorption device comprising a plurality of electrically controllable piezoelectric tongues positioned along said longitudinal direction of said slit forming a corresponding number of sections of said planar X-ray beam, each of said tongues having a fixed end and a free end, a control device for feeding electrical control signals to said tongues for continuous vibration thereof at a predetermined frequency.

The invention also relates to a method for operating a slit radiography apparatus provided with an absorption device which interacts with a slit diaphragm and which comprises electrically controllable piezoelectric tongues, each having a fixed end and a free end and a control device which feeds electrical control signals to said tongues during operation, said method comprising feeding control signals to said tongues for continuous vibration thereof at a predetermined frequency.

Such an apparatus is known, for example, from Dutch Patent Applications 8400845 and 8601678. The apparatus known from Dutch Patent Application 8400845 comprises an X-ray source which is capable of scanning a patient or object to be examined with a flat fan-shaped X-ray beam via a slit-type diaphragm. In order to obtain an equalised X-ray image, an absorption device comprising a number of adjacently situated absorption elements which can be brought into the X-ray beam to a greater or lesser extent under the control of electrical control signals is provided near the slit diaphragm.

Each absorption element can affect a sector of the fan-shaped X-ray beam. The control signals are obtained by means of a detector which is provided behind the patient or the object and which measures the amount of radiation transmitted for each sector of the X-ray beam and provides a corresponding electrical control signal.

As absorption elements, use could be made of piezoelectric material which is clamped at one end and whose other end can be swivelled into the X-ray beam under the control of the abovementioned electrical control signals. Such tongues already absorb X-ray radiation to a certain extent themselves, but they are usually also provided with special elements which absorb X-ray radiation at the free ends. In the latter case, it is sufficient if the special elements which absorb X-ray radiation can be swivelled into the X-ray beam.

The tongues may be simple tongues of piezoelectric material which can be brought into a curved state by means of an electrical control voltage applied between the top and bottom face. The tongues may also be so-called bimorphous elements which are composed of two strips of piezoelectric material laid one on top of the other. The electrical control voltage may then be applied between the interconnected outer faces (top and bottom face) and the common central face.

The tongues can be controlled in such a manner that the position of the tongues with respect to the slit of the slit diaphragm is always matched to the amount of radiation instantaneously transmitted through the patient or the object in the associated sector of the X-ray beam, that is to say, to the instantaneous, and therefore local, transmissivity of the patient for the object.

In the Dutch Patent Application 8601678, the contents of which are regarded as included here by reference, a description is given of another method, according to which a so-called hardness modulation of the X-ray beam is used.

According to the method known from the Dutch Patent Specification 8601678, the free ends of the tongues or the absorbing elements vibrate continuously at a predetermined frequency between a position completely or largely clearing the slit diaphragm and a position completely or largely blocking the slit. The amount of radiation instantaneously transmitted in a sector of the X-ray beam is controlled by varying the phase and/or amplitude of the vibration as a function of the instantaneous transmissivity of the patient or the object in the sector concerned.

In all cases it is important that the tongues respond rapidly and accurately to the electrical control signals. Thus, for example, it is important in the abovementioned Dutch Patent Application 8601678 to be able to match the phase of the vibrating tongues rapidly to the instantaneous local transmissivity of the patient or of the object. Uncontrolled vibrations should also be prevented.

The object of the invention is therefore to provide an apparatus of the type described above which meets the requirements mentioned. For this purpose, according to the invention, such an apparatus is characterised by at least one stop element for limiting the maximum deflections of at least a number of said tongues, by said control signals being of such magnitude that said tongues are limited in their deflections by said at least one stop element for at least part of the time of any vibration period and by means for changing phases of said electrical control signals during said part of the time of said vibration periods.

It is being observed that a stop element in a slit radiography apparatus is known as such from WO-A-8902645.

The invention will be described in greater detail below with reference to the attached drawing.

FIGS. 3 to 6 inclusive show diagrammatically a number of exemplary embodiments of stop devices for piezoelectric tongues of an apparatus according to the invention.

Figure 1:
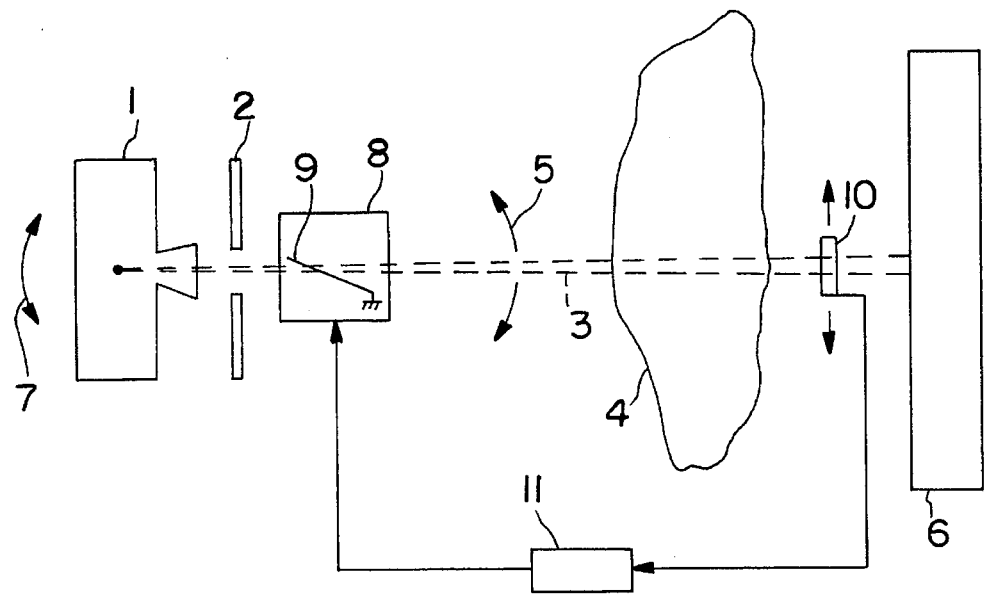
FIG. 1 shows, diagrammatically in side view, an example of a slit radiography apparatus provided with an absorption device having piezoelectric tongues.

FIG. 1 shows, diagrammatically in side view, an example of a (known) slit radiography apparatus provided with an absorption device. The apparatus shown comprises an X-ray source 1 which is capable of scanning a patient 4 or an object to be examined with a flat fan-shaped X-ray beam 3 in the direction, indicated by arrows 5, transverse to the plane of the fan-shaped beam 3 via a slit-type diaphragm 2. An X-ray detector 6, which may comprise, for example an X-ray film cassette or a concomitantly moving elongated X-ray image intensifier tube, picks up the radiation transmitted through the patient and ensures the formation of the desired X-ray shadow image. The scanning in accordance with the arrows 5 takes place because, during operation, the X-ray source with the diaphragm 2 swivels about an axis extending transversely to the plane of the drawing, preferably through the X-ray focus of the X-ray source, as indicated by an arrow 7.

To obtain an equalised radiogram, an absorption device 8 is used which is capable of modulating the X-ray beam in each sector and which also swivels concomitantly with the X-ray source. The absorption device comprises adjacently situated piezoelectric tongues 9, also termed piezoceramic tongues because the tongues are produced from ceramic material having piezoelectric properties. Each tongue is able to affect a certain sector of the X-ray beam 3. For this purpose, the tongues are mounted in a fixed manner, for example clamped, at one end. By feeding suitable electrical control signals to a tongue, it bends, with the result that the free end penetrates the X-ray beam. The required control signals are provided by a detector 10 which is situated in this example between the patient and the X-ray detector and which picks up the radiation transmitted through the patient at each instant and provides electrical signals for each sector of the X-ray beam which are fed via a processing circuit 11 to the corresponding tongues. As shown, the detector may be an elongated radiation detector moving synchronously with the scanning movement of the X-ray beam, but it may also be a two-dimensional stationary detector.

Figure 2:
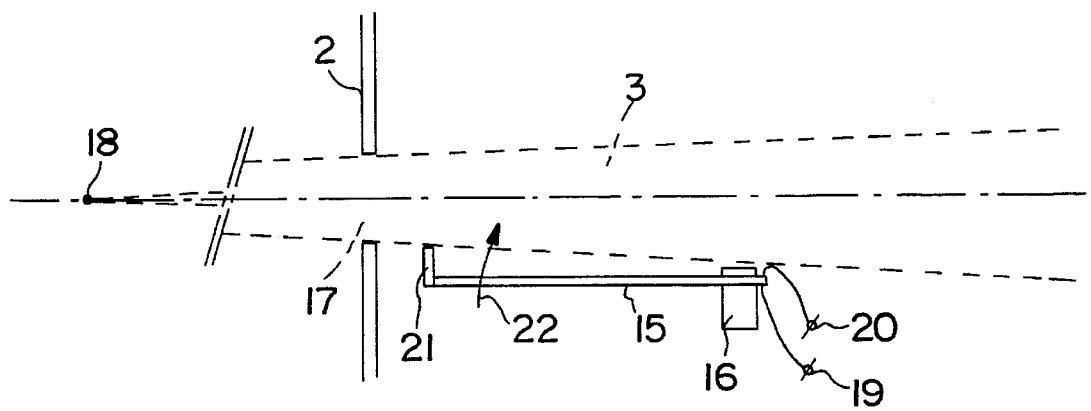
FIG. 2 shows, diagrammatically in side view, a piezoelectric tongue in relation to the slit of the slit diaphragm of a slit radiography apparatus according to the invention.

FIG. 2 shows, diagrammatically in side view, a piezoelectric tongue 15 which is suitably clamped in a fixed manner near one of the ends in a support 16. The other end is free and is situated near the slit 17 of the slit diaphragm 2. The piezoelectric tongue is shown in the rest position in which the slit 17 is left completely free. This means that the X-ray beam 3 originating from the X-ray focus 18 of the X-ray source 7 not shown in greater detail in FIG. 2 is able to pass the slit and the tongues freely.

The piezoelectric tongues are provided with diagrammatically shown connecting terminals 19,20 for feeding electrical control signals. Moreover, in the example shown, the piezoelectric tongues are provided with an absorption element 21 at the free ends. By means of a suitable control voltage the result can be achieved that a piezoelectric tongue assumes a bent position such that the free end or the absorption element moves to a greater or lesser extent into the X-ray beam, as is indicated by an arrow 22. As soon as the absorption element extends into the X-ray beam, the X-ray radiation is at least partially absorbed, and therefore attenuated, at the position of the absorption element.

As already pointed out earlier, it is important that the tongues follow the control signals rapidly and accurately. The speed at which the position of a tongue can be altered is related to the mass inertia or the mechanical resonance frequency of the tongue. A large mass inertia opposes rapid changes of position or vibration phase. Although supplying stronger control signals may result in a more rapid response of the tongues, it also increases the risk of overshoot and of damage to the tongue. A tongue having a relatively low mechanical resonance frequency, that is to say, a resonance frequency which is in the same order of magnitude as the frequencies occurring in the control signals, may also enter into uncontrolled vibration and, for example, break as a result.

According to the invention, the problems outlined can be eliminated by using a stop device which limits the maximum deflection of a tongue or of a tongue section during operation.

Figure 3:
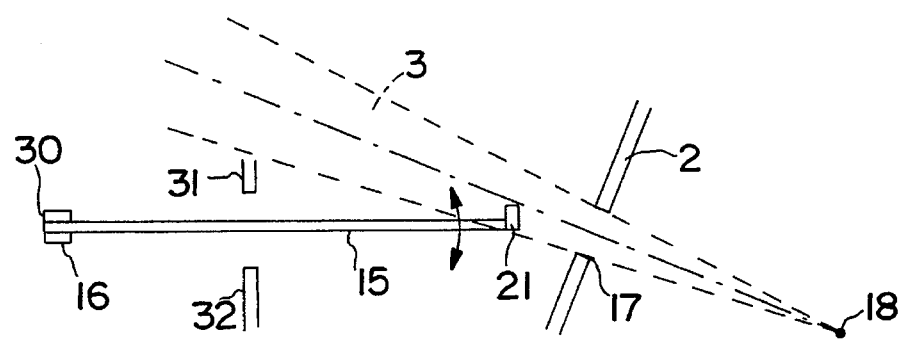

FIG. 3 shows diagrammatically a first example of such a stop device. The stop device shown comprises two stop elements 31,32 which are provided on either side of the tongue 15 at a distance from the end 30 clamped in a support 16 and which limit the maximum deflection of the tongue. As soon as the tongue collides with a stop element 31 or 32, said stop element acts as a fixed point which temporarily takes over the function of the support 16. The length of a tongue is consequently, as it were, reduced, as a result of which the resonance frequency becomes higher. The tongue consequently becomes more rapidly controllable.

The stop elements may have various forms and be produced, at least insofar as they lie in the region of the X-ray beam 3, from a material which is transparent to X-ray radiation, for example plexiglass.

Figure 4:
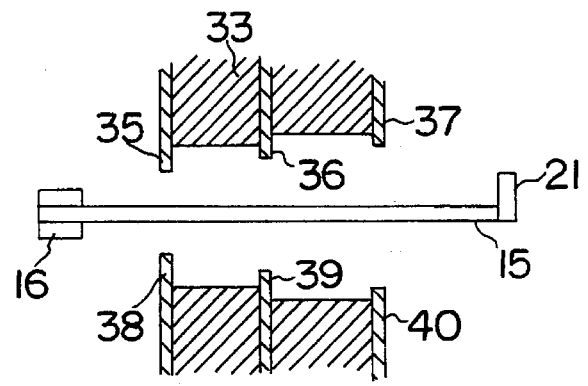

FIG. 4 shows an exemplary embodiment of stop elements 33,34 which each comprise a number of stop strips situated at a distance from each other along each of the tongues 15 in the form of ribs 35,36,37, or 38,39,40, respectively. As the deflection of a tongue 15 increases, it collides first with the stop ribs 35,38, then with the stop ribs 36,39 and finally, with the stop ribs 37,40. At the same time, the mechanical resonance frequency of the tongue increases as it rests against more stop ribs.

Figure 5:
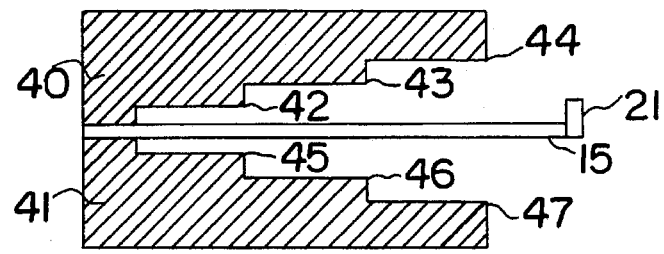

The stop elements may alternatively be strips placed in step form which form stop edges as shown in FIG. 5. The stop elements 40a, 41 shown in FIG. 5 each have three stop edges 42,43,44, or 45,46,47, respectively. In addition, the stop elements in this example also form the tongue support. In the exemplary embodiments of FIGS. 3 to 5 inclusive, the stop elements form discrete stop ribs or edges. The stop elements may, however, also have, at least partially, a smooth shape, for example a shape according to a quadratic curve or a cubic curve or even according to a combination of different types of curves. A combination of partially smoothly shaped stop elements and one or more discrete stop edges is also possible.

Figure 6:
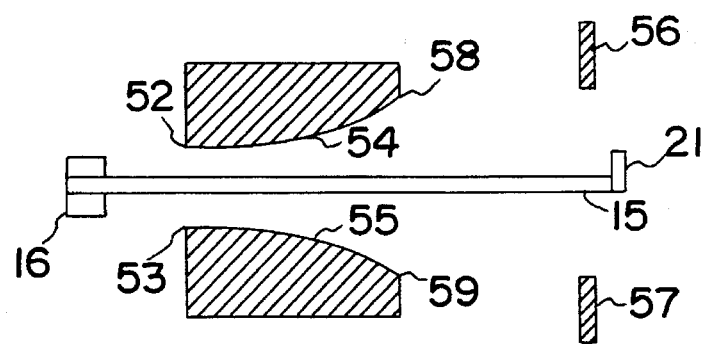

FIG. 6 shows an example of stop elements 50,51 which, viewed from the clamped end of the tongues 15, first form a stop edge 52 or 53, respectively, and then have a smoothly shaped section 54 or 55, respectively. In combination with the smooth sections 54,55, discrete stops 56,57 which are capable of interacting with a part of the tongues situated near the free ends of the tongues have moreover also been provided in this example.

The rear edges 58,59 of the stop elements 54,55 may optionally come into contact with the tongues as required during the operation of the apparatus and therefore function optionally as discrete stop edges.

In the examples shown, the stop elements are symmetrically arranged on either side of the tongues. This is not, however, necessary. Thus, for example, the embodiment of FIG. 3 could be modified in a manner such that the stop element 32 is situated further from the rest position and/or further from the clamped end of the tongue than the stop element 31.

In principle, the stop element at one side of the tongues could even be completely omitted, with the result that the deflection of the tongues is limited only on one side.

Since the properties of the individual tongues exhibit the greatest mutual differences at the maximum deflection of the tongues, the tongues are preferably so arranged that the free ends of the tongues are situated outside the X-ray beam at the maximum deflection. That is to say, the free end of a tongue moves, at large deflection, behind the slit 17 of the fixed parts limiting the slit diaphragm and change direction of movement at that point.

It is pointed out that, after the above, various modifications are obvious to the person skilled in the art. Thus, stop elements having a smooth shape as shown in FIG. 5 may also form the support, as shown in FIG. 4. Moreover, instead of three stop ribs or edges, more or less stop ribs or edges may also be used, optionally in combination with one or more smoothly shaped stop sections. These and similar modifications are considered to fall within the scope of the invention.

I claim:

1. An absorption assembly for slit radiography apparatus including an X-ray source, a slit diaphragm and an X-ray detector wherein said absorption assembly is disposed between said X-ray source and said X-ray detector, which comprises:

a plurality of piezoelectric tongues each having a fixed end and a free end including an absorption element;

stop means for limiting individually deflection of each of said piezoelectric tongues, said stop means being comprised of a first stop strip and a second stop strip disposed behind said first stop strip, a distance between said second stop strip and a rest position of said piezoelectric tongues being greater than a distance between said first stop strip and a rest position of said piezoelectric tongues.

2. The absorption assembly as defined in claim 1 wherein said stop strips are parallelly-disposed rib members.

3. The absorption assembly as defined in claim 1 wherein said stop strips are edges of stop elements in stepped configuration.

4. The absorption assembly as defined in claim 1 wherein stop means are positioned on either side of said plurality of piezoelectric tongues.

5. The absorption assembly as defined in claim 1 wherein stop means are asymmetrically positioned on either side of said plurality of piezoelectric tongues.

* * * * *